US009618749B2

(12) United States Patent
Deleeuw et al.

(10) Patent No.: US 9,618,749 B2
(45) Date of Patent: Apr. 11, 2017

(54) NAUSEA AND SEIZURE DETECTION, PREDICTION, AND MITIGATION FOR HEAD-MOUNTED DISPLAYS

(71) Applicant: Intel Corporation, Santa Clara, CA (US)

(72) Inventors: William C. Deleeuw, Portland, OR (US); Jeffrey C. Sedayao, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/129,647

(22) PCT Filed: Aug. 30, 2013

(86) PCT No.: PCT/US2013/057561
§ 371 (c)(1),
(2) Date: Dec. 27, 2013

(87) PCT Pub. No.: WO2015/030797
PCT Pub. Date: Mar. 5, 2015

(65) Prior Publication Data
US 2016/0178904 A1 Jun. 23, 2016

(51) Int. Cl.
*G02B 27/01* (2006.01)
*G06F 1/16* (2006.01)
(Continued)

(52) U.S. Cl.
CPC ......... *G02B 27/0172* (2013.01); *G06F 1/163* (2013.01); *G06F 3/011* (2013.01);
(Continued)

(58) Field of Classification Search
CPC . A61B 5/4094; A61B 5/42; G02B 2027/0112; G02B 2027/0118;
(Continued)

(56) References Cited

U.S. PATENT DOCUMENTS

2010/0141555 A1* 6/2010 Rorberg ............... G02B 27/017
345/8
2012/0182206 A1 7/2012 Cok et al.
2012/0197092 A1 8/2012 Luo et al.

FOREIGN PATENT DOCUMENTS

JP 08220470 A 8/1996
JP 2000312319 A 11/2000
JP 2003279882 A 10/2003

OTHER PUBLICATIONS

International Search Report and Written Opinion received for International Application No. PCT/US2013/057561, mailed May 22, 2014, 14 pages.

(Continued)

*Primary Examiner* — Dmitriy Bolotin
(74) *Attorney, Agent, or Firm* — Barnes & Thornburg LLP

(57) ABSTRACT

Technologies for mitigating a physiological condition include a wearable computing device coupled with a head-mounted display and sensor(s). The wearable computing device may receive sensor data indicative of a physical attribute of the user while displaying information on the head-mounted display. The wearable computing device analyzes the sensor data to detect a physiological condition of the user and, if detected, applies a mitigation strategy to mitigate the physiological condition. The detected physical condition may be a nausea condition or a seizure condition. To reduce potential risk to the user, the wearable computing device may buffer information to be displayed by the head-mounted display, analyze the display information based on risk factor rules to determine whether the display information presents a potential risk to the user, and reduce the display rate of the head-mounted display in response to the potential risk to the user. Other embodiments are described and claimed.

25 Claims, 5 Drawing Sheets

(51) Int. Cl.
*G06F 3/01* (2006.01)
*H04N 13/00* (2006.01)
*H04N 13/04* (2006.01)
*A61B 5/00* (2006.01)

(52) U.S. Cl.
CPC ......... *G06F 3/013* (2013.01); *H04N 13/0033* (2013.01); *H04N 13/044* (2013.01); *H04N 13/0468* (2013.01); *H04N 13/0497* (2013.01); *A61B 5/4094* (2013.01); *A61B 5/42* (2013.01); *G02B 27/017* (2013.01); *G02B 2027/014* (2013.01); *G02B 2027/0112* (2013.01); *G02B 2027/0118* (2013.01); *G02B 2027/0127* (2013.01); *H04N 2213/002* (2013.01)

(58) Field of Classification Search
CPC ...... G02B 2027/0127; G02B 2027/014; G02B 27/017; G02B 27/0172; G02B 27/02; G06F 1/00; G06F 1/163; G06F 3/011; G06F 3/013; H04N 13/0033; H04N 13/044; H04N 13/0468; H04N 13/0497; H04N 2213/002

USPC .......................................................... 345/8
See application file for complete search history.

(56) References Cited

OTHER PUBLICATIONS

"Optical head-mounted display," Wikipedia, The Free Encyclopedia, retrieved from: <http://en.wikipedia.org/w/index.php?title=Optical_head-mounted_display&oldid=570809674>, edited Aug. 30, 2013, 14 pages.

"Head-mounted display," Wikipedia, The Free Encyclopedia, retrieved from: <http://en.wikipedia.org/w/index.php?title=Head-mounted_display&oldid=547331216>, edited Mar. 27, 2013, 7 pages.

Nijsen, "Accelerometry based detection of epileptic seizures," Doctoral Thesis, Sep. 11, 2008, 136 pages.

Nam et al., "Automatic Detection of Nausea Using Bio-Signals During Immerging in A Virtual Reality Environment," Papers from 23rd Annual International Conference of the IEEE Engineering in Medicine and Biology Society, Oct. 25-28, 2001, 5 pages.

* cited by examiner

NAUSEA AND SEIZURE DETECTION, PREDICTION, AND MITIGATION FOR HEAD-MOUNTED DISPLAYS

CROSS REFERENCE TO RELATED APPLICATIONS

This application is a national stage entry under 35 USC §371(b) of International Application No. PCT/US2013/057561, which was filed Aug. 30, 2013.

BACKGROUND

Head-mounted displays for computer systems position computer-generated visual information close to a user's eyes. Many head-mounted displays use a translucent display or only partially cover the user's field of vision, allowing computer information to overlay the user's normal vision. Such head-mounted displays typically provide informational overlays, which may respond to the user's current context. Head-mounted displays may render computer-generated visual features that appear to be integrated with the user's environment, also referred to as "augmented reality." Other head-mounted displays may completely cover the user's field of vision with computer-generated visual features, for example in "virtual reality" applications.

Current head-mounted displays are known to induce nausea in many users. Typically, there is a small amount of latency between the user's head movements and the responsive display of objects on the head-mounted display. For many users, that latency induces motion sickness and/or nausea. Head-mounted displays may also induce nausea by rendering motion that is different from the user's true motion. For example, moving forward in a virtual space while standing still in reality may induce motion sickness and/or nausea. The incidence of nausea may increase with the length of time the head-mounted display is in use.

Additionally, head-mounted displays may increase the risk of seizure in some users. For example, a certain proportion of the population with epilepsy is photosensitive; that is, for some users, exposure to flashing lights or to certain visual patterns may trigger seizures. In particular, flashing lights at a frequency between five and thirty flashes per second is known to trigger seizures in some persons. Even where seizures are not triggered, some photosensitive persons may experience other symptoms such as headache, nausea, or dizziness. Head-mounted displays—like any other display technology—may generate flashes or visual patterns capable of triggering seizures or other physical problems.

Nausea and seizure may be detected in real time by analyzing sensor data that monitors the physiological state of the user. Nausea is known to change the user's skin conductivity (galvanic skin response, or "GSR"), skin temperature, pulse rate, and possibly eye blink rate. Nausea may also be detected through measurement of the user's motor stability. Similarly, seizure may be detected by measuring the user's motor activity for events such as falling or trembling, or through eye gaze tracking.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
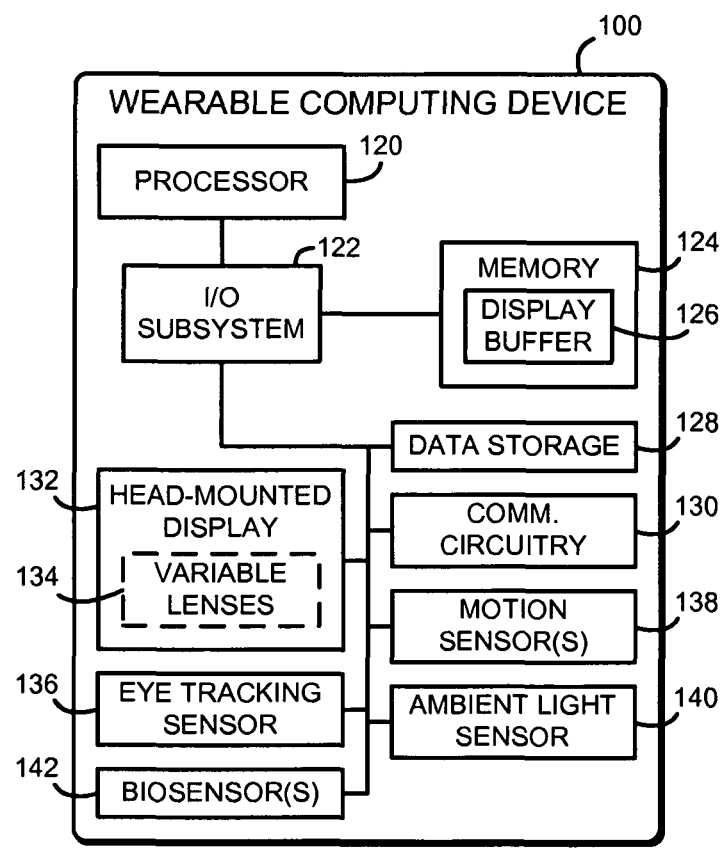
FIG. 1 is a simplified block diagram of at least one embodiment of a wearable computing device for nausea and seizure detection, prediction, and mitigation.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative wearable computing device 100 detects and predicts physiological conditions such as nausea and seizure in a user of the wearable computing device 100, and may apply a variety of mitigation strategies to mitigate the physiological condition or reduce risk to the user. The wearable computing device 100 may use a number of sensors to monitor the physiological state of the user and/or the state of the environment, and use the sensor data to detect physiological conditions of the user. Additionally or alternatively, the wearable computing device 100 may monitor information displayed to the user to predict potential risk to the user, including risk of seizure and risk for information overload. Integrating physiological condition prediction, detection, and mitigation into head-mounted display technology—particularly when used with a wearable computing device—may allow such technology to be used by a segment of the population that is currently physically unable to use it. Further, although the disclosed technologies are particularly suited for head-mounted displays, they are potentially usable for other wearable computing devices. For example, active-shutter stereoscopic glasses used for viewing three-dimensional movies or television may also perform nausea and/or seizure detection, prediction, and mitigation.

The wearable computing device 100 may be embodied as any type of computing device capable of detecting, predicting, and mitigating nausea or seizure and otherwise performing the functions described herein. For example, the wearable computing device 100 may be embodied as, without limitation, a head-mounted display, smart eyeglasses, a smart watch, a smart phone, a computer, a tablet computer, a laptop computer, a notebook computer, a mobile computing device, a cellular telephone, a handset, a messaging device, a distributed computing system, a multiprocessor system, a processor-based system, a consumer electronic device, a digital television device, and/or any other computing device configured to detect, predict, and/or mitigate harm to the user. As shown in FIG. 1, the illustrative wearable computing device 100 includes a processor 120, an I/O subsystem 122, a memory 124, a data storage 128, communication circuitry 130, and a head-mounted display 132. Of course, the wearable computing device 100 may include other or additional components, such as those commonly found in a computer (e.g., various input/output devices), in other embodiments. Additionally, in some embodiments, one or more of the illustrative components may be incorporated in, or otherwise form a portion of, another component. For example, the memory 124, or portions thereof, may be incorporated in the processor 120 in some embodiments.

The processor 120 may be embodied as any type of processor capable of performing the functions described herein. For example, the processor 120 may be embodied as a single or multi-core processor(s), digital signal processor, microcontroller, or other processor or processing/controlling circuit. Similarly, the memory 124 may be embodied as any type of volatile or non-volatile memory or data storage capable of performing the functions described herein. In operation, the memory 124 may store various data and software used during operation of the wearable computing device 100 such as operating systems, applications, programs, libraries, and drivers. The memory 124 additionally includes a display buffer 126, which temporarily stores image data that will be displayed by the head-mounted display 132. The display buffer 126 may be a dedicated portion of the memory 124, or in some embodiments may be a separate pool of memory dedicated to the head-mounted display 132, such as a video ram (VRAM) buffer. The memory 124 is communicatively coupled to the processor 120 via the I/O subsystem 122, which may be embodied as circuitry and/or components to facilitate input/output operations with the processor 120, the memory 124, and other components of the wearable computing device 100. For example, the I/O subsystem 122 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 122 may form a portion of a system-on-a-chip (SoC) and be incorporated, along with the processor 120, the memory 124, and other components of the wearable computing device 100, on a single integrated circuit chip.

The data storage 128 may be embodied as any type of device or devices configured for the short-term or long-term storage of data. For example, the data storage 128 may include any one or more memory devices and circuits, memory cards, hard disk drives, solid-state drives, or other data storage devices. In some embodiments, the data storage 128 may provide a backing store for the information stored in the display buffer 126.

The communication circuitry 130 of the wearable computing device 100 may be embodied as any communication circuit, device, or collection thereof, capable of enabling communications between the wearable computing device 100 and other remote devices. The communication circuitry 130 may be configured to use any one or more communication technology (e.g., wireless or wired communications) and associated protocols (e.g., Wideband Code Division Multiple Access (W-CDMA), Global System for Mobile Communications (GSM), Bluetooth®, Wi-Fi®, WiMAX, Ethernet, etc.) to effect such communication.

The head-mounted display 132 of the wearable computing device 100 may be embodied as any type of display mountable to the user's head and capable of projecting digital visual information in the user's field of vision. In some embodiments, the head-mounted display 132 may be transparent or semitransparent and thus capable of displaying information in a portion of the user's field of vision without obscuring the rest of the user's vision. Such partial displays are known as display overlays, or simply overlays. In some embodiments, the head-mounted display 132 may include a display source such as a liquid crystal display (LCD) or a light emitting diode (LED) array that projects display information onto a small, clear or translucent prismatic display screen positioned in front of the user's eye. A similar screen may be used for the other eye. The use of one screen for each eye may allow for stereoscopic depth effects. In another embodiment, the head-mounted display 132 may include goggles that fully block external light from reaching the user. One or a pair of LCD or LED displays may be positioned on the inside of the goggles to produce the display.

In some embodiments, the head-mounted display 132 may include one or more variable lenses 134. The variable lenses 134 are configurable to allow or block variable amounts of environmental light from being transmitted through the head-mounted display 132 to reach the user. For example, in an active-shutter stereoscopic display glasses, the variable lenses 134 may be configured to rapidly alternate between blocking all light and allowing all light. The variable lenses 134 may be embodied as a thin liquid crystal layer positioned in the user's field of vision that becomes opaque to light in response to an electrical signal.

The wearable computing device 100 also includes a number of sensors to detect features of the environment and/or the user such as, for example, an eye tracking sensor 136, one or more motion sensor(s) 138, an ambient light sensor 140, and one or more biosensors 142. Of course, the wearable computing device 100 may include additional or other sensors in other embodiments.

The eye tracking sensor 136 may be embodied as any one or more sensors capable of determining a direction in which the user's gaze is directed, which may include whether the user is focused on the head-mounted display 132. For example, in some embodiments, the eye tracking sensor 136 may use active infrared emitters and infrared detectors to track the viewer's eye movements over time. The eye tracking sensor 136 may capture the infrared light reflected off of various internal and external features of the viewer's eye and thereby calculate the direction of the viewer's gaze. In other embodiments, the eye tracking sensor 136 may be embodied as a video camera capable of recording the user's eye motion. Additionally, in some embodiments, the eye tracking sensor 136 may be capable of detecting blinks or other behavior of the user's eye.

The motion sensor(s) 138 may be embodied as one or more of any sensor capable of sensing motion of the wearable computing device 100 and/or the head-mounted display 132 including, for example, one or more accelerometers, gyroscopes, compasses, or any other type of device or devices capable of detecting device motion. For example, the motion sensor(s) 138 may include a three-axis accelerometer and a three-axis gyroscope, allowing motion tracking in three linear dimensions and about three rotational axes.

The ambient light sensor 140 may be embodied as any sensor capable of detecting or measuring the amount of light in the environment of the wearable computing device 100. For example, the ambient light sensor 140 may be embodied as a CMOS photodiode. In other embodiments, the ambient light sensor 140 may be incorporated in another sensor such as a camera or the eye tracking sensor 136.

The biosensors 142 may include any sensor that measures a physiological attribute of the user of the wearable computing device 100. In some embodiments, the biosensors 142 may include a galvanic skin response (GSR) sensor. The GSR sensor includes at least a pair of electrodes that, when placed in contact with the user's skin, measure the electrical conductance of the skin. Electrical conductance of the skin varies with the skin's moisture level, and thus may indicate activity of the sweat glands, which in turn is may indicate the existence of a physiological or psychological condition. Additionally, in some embodiments the biosensors 142 may include a thermometer to measure body temperature of the user. Still further, in some embodiments, the biosensors 142 may include a pulse sensor to detect the pulse rate of the user, for example by measuring minute color changes in the user's skin and/or eyes caused by pulsing blood. Additionally or alternatively, existing sensors may be used as biosensors 142; for example, an existing camera (e.g., a camera used as the eye tracking sensor 136) may be used as a pulse sensor, or the blink rate of the user may be measured by the eye tracking sensor 136. One or more of the biosensors 142 may be mounted on the head-mounted display 132, allowing the biosensors 142 to have direct contact to the skin or other features of the user.

Figure 2:
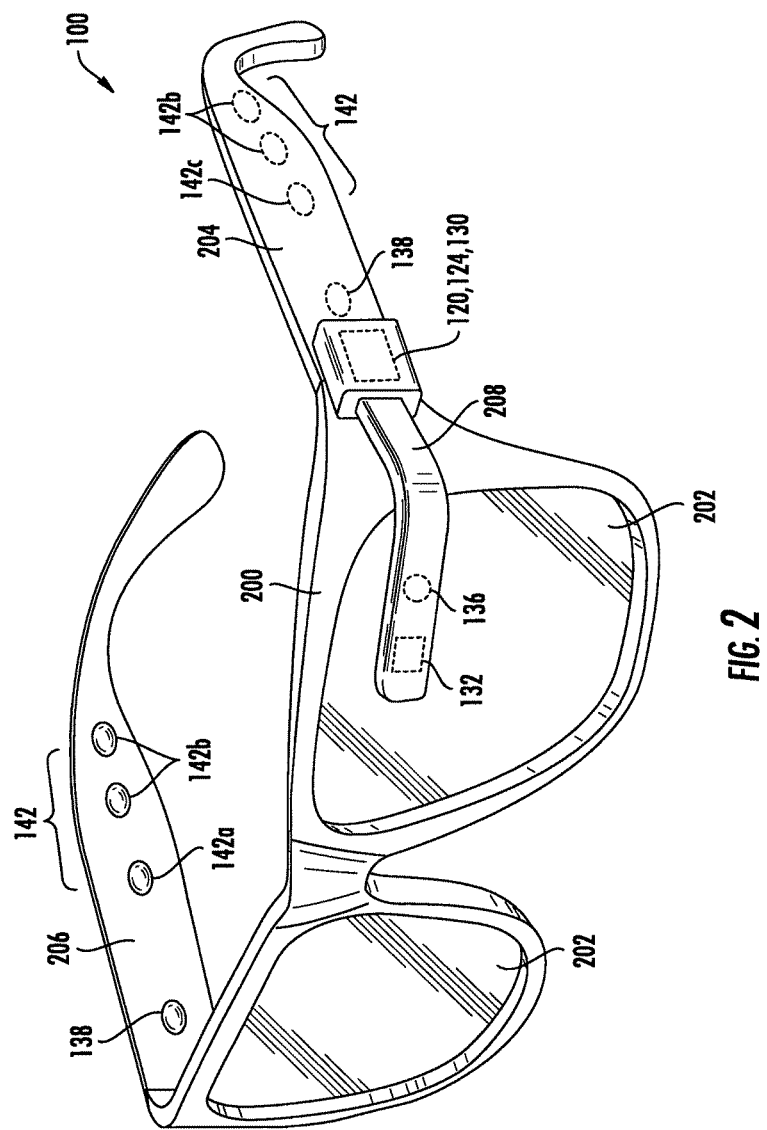
FIG. 2 is a perspective view of at least one embodiment of the wearable computing device of FIG. 1.

Referring now to FIG. 2, a perspective view of one embodiment of a wearable computing device 100 is shown. In FIG. 2, the wearable computing device 100 is illustrated as a pair of smart eyeglasses. The eyeglasses include a frame 200 surrounding a pair of lenses 202. The frame 200 is connected to a left temple 204 that extends back from the frame 200. The other side of the frame 200 is connected to a right temple 206 that extends back from the frame 200. In use, the frame 200 and temples 204, 206 contact the skin of the user's head and secure the eyeglasses in front of the user's face.

The left temple 204 further includes a forward extension bracket 208 covering a portion of one of the lenses 202 within the field of view of the user. The head-mounted display 132 is mounted on the extension bracket 208, within the user's field of view. All or a portion of the extension bracket 208 may be constructed of transparent or translucent material, allowing the head-mounted display 132 to generate display overlays in the user's field of vision. The eye tracking sensor 136 is also mounted on the extension bracket 208, allowing the motion of the user's eye to be tracked. Other components of the wearable computing device 100, including the processor 120, the memory 124, and the communication circuitry 130, are mounted within the left temple 204.

In the illustrative embodiment, the temples 204, 206 include the motion sensor(s) 138, embodied as an integrated three-axis accelerometer/gyroscope and as a digital compass. The temples 204, 206 further include biosensors 142 mounted on the inner surfaces of the temples 204, 206, allowing direct skin contact with the user. Illustratively, the biosensor 142a is a thermometer, biosensors 142b are galvanic skin response sensors (each including a pair of electrodes), and the biosensor 142c is a pulse detector. Of course, in other embodiments, additional or other sensors may be attached to, or otherwise incorporated in the frame 200 and/or the temples 204, 206 in various locations.

Figure 3:
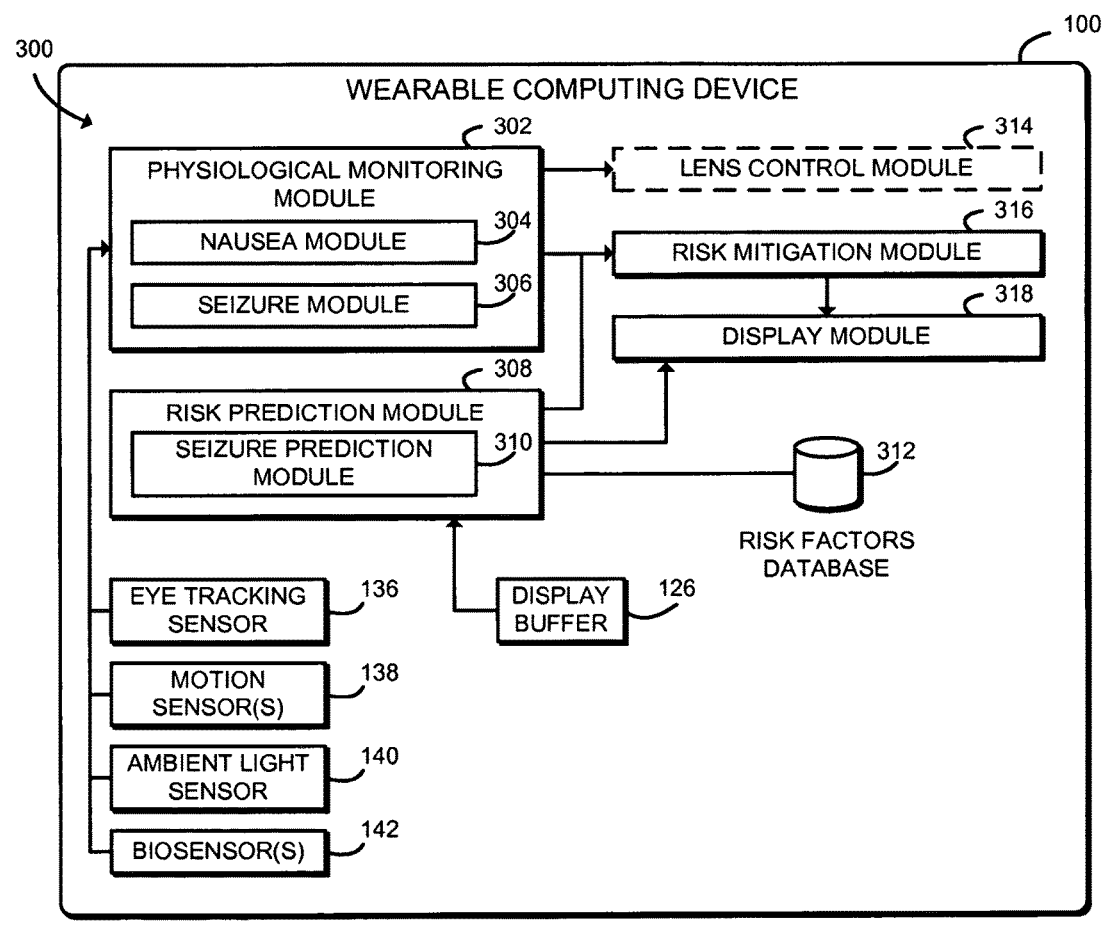
FIG. 3 is a simplified block diagram of at least one embodiment of an environment of the wearable computing device of FIGS. 1-2.

Referring now to FIG. 3, in an embodiment, the wearable computing device 100 establishes an environment 300 during operation. The illustrative environment 300 includes a physiological monitoring module 302, a risk prediction module 308, a risk factors database 312, a risk mitigation module 316, and a display module 318. Some embodiments may also include a lens control module 314. The various modules and sub-environments of the environment 300 may be embodied as hardware, firmware, software, or a combination thereof.

The physiological monitoring module 302 is configured to receive data from one or more sensors of the wearable computing device 100 and to detect the presence of a physiological condition such as nausea or seizure. The physiological monitoring module 302 may analyze sensor data from any combination of the eye tracking sensor 136, the motion sensor(s) 138, and/or the biosensor(s) 142. The physiological monitoring module 302 may also detect a potential seizure condition based on sensor data that monitors the user's environment, such as the ambient light sensor 140. In some embodiments, those functions may be performed by sub-modules, such as a nausea module 304 or a seizure module 306.

The risk prediction module 308 is configured to analyze data from the display buffer 126 that is to be displayed on the head-mounted display 132, and predict potential risk to the user. Potential risk to the user includes potential seizure, as well as the potential that information is displayed on the head-mounted display 132 at a rate that is too fast to be consumed by the user. In contrast to the physiological monitoring module 302, the risk prediction module 308 does not analyze sensor data of the wearable computing device 100. Rather, the risk prediction module 308 applies rules from the risk factors database 312 to the display information to determine potential risk. For example, in the illustrative embodiment, the risk factors database 312 includes a set of rules defining display information that may be dangerous to humans and defining data rates that may be consumed by humans. Each of the rules may be embodied as a policy defining safe display information or potentially dangerous display information. For example, a rule may define that display information containing periodic flashes of intensity at a frequency between five Hz and thirty Hz may be dangerous. In some embodiments, the functions of the risk prediction module 308 may be performed by sub-modules, such as a seizure prediction module 310.

As discussed above, the environment 300 may include the lens control module 314. In such embodiments, the lens control module 314 is configured to adjust the amount of environmental light transmitted through the variable lenses 134 in response to a control signal from the physiological monitoring module 302 and/or the risk mitigation module 316. Reducing the amount of environmental light transmitted to the user or eliminating combinations of environmental and displayed light may mitigate the risk of a potential seizure condition caused by environmental light.

The risk mitigation module 316 is configured to apply various mitigation strategies to alleviate or reduce the risk of a physiological condition detected by the physiological monitoring module 302 and/or the risk prediction module 308. As described below, mitigation strategies may include suspending or hiding display overlays on the head-mounted display 132, reducing the density, intensity, saturation, or resolution of display overlays on the head-mounted display 132, or reducing the update rate of the head-mounted display 132. Other mitigation strategies may be appropriate for particular embodiments of the head-mounted display 132, for example, displaying information in one eye only or reducing environmental light transmitted through the head-mounted display 132 via the lens control module 314.

The display module 318 is configured to display information to the user on the head-mounted display 132. The display module 318 receives the display information from the display buffer 126, mediated by the risk prediction module 308. The display information input to the display buffer 126 may be generated by one or more applications (not shown) executing on the wearable computing device 100. The display module 318 may respond to the mitigation strategies applied by the risk mitigation module 316.

Figure 4:
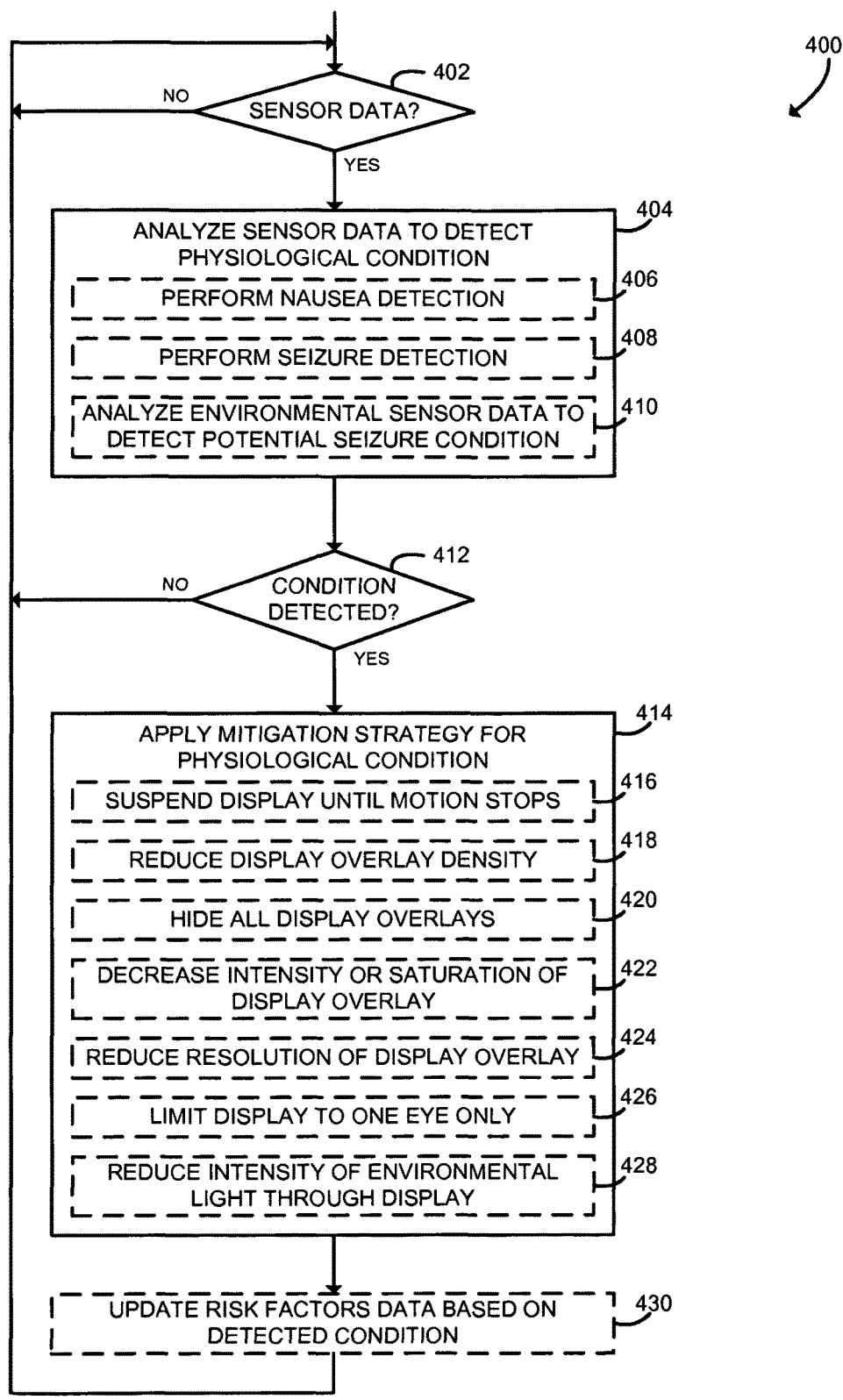
FIG. 4 is a simplified flow diagram of at least one embodiment of a method for mitigating a physiological condition of a user of a head-mounted display, which may be executed by the computing device of FIGS. 1-3.

Referring now to FIG. 4, in use, the wearable computing device 100 may execute a method 400 for nausea or seizure detection and mitigation. The method 400 begins with block 402, in which the wearable computing device 100 determines whether sensor data is available for analysis. The wearable computing device 100 may poll and/or handle interrupts from any number of sensors, including the eye tracking sensor 136, the motion sensor(s) 138, the ambient light sensor 140, and/or the biosensor(s) 142. In particular, the wearable computing device 100 may monitor the sensors while one or more display overlays are shown on the head-mounted display 132. If no sensor data is available for analysis, the method 400 loops back to block 402 to continue monitoring for sensor data. If sensor data is available, the method 400 advances to block 404.

In block 404, the wearable computing device 100 analyzes the sensor data to detect one or more physiological conditions exhibited by the user. The physiological conditions may be electronically detectable in the sensor data in advance of the user showing overt signs of the physiological condition. In some embodiments, in block 406, the wearable computing device 100 detects a nausea condition based on the sensor data. As described above, nausea tends to produce characteristic patterns within the sensor data. For example, nausea is associated with changes to heart rate, skin conductance, skin temperature, and blink rate. The wearable computing device 100 may perform statistical or frequency analysis on incoming sensor data to determine whether characteristic nausea signals are present. In some embodiments, in block 408 the wearable computing device 100 detects a seizure condition based on the sensor data. As described above, seizure tends to produce characteristic patterns within the sensor data. For example, seizure is associated with changes to heart rate, skin conductance, skin temperature, blink rate, gaze position, and repetitive motion. The wearable computing device 100 may perform statistical or frequency analysis on incoming sensor data to determine whether characteristic seizure signals are present.

In some embodiments, in block 410, the wearable computing device 100 may analyze environmental sensor data to detect a potential seizure condition. In contrast to the sensor data analyzed in blocks 406, 408, environmental sensor data corresponds to physical phenomena in the user's environment rather than characteristics of the user. For example, as described above, seizure may be caused in some users by flickering or pulsating light in a particular frequency range. Such flickering or pulsating light may be caused by an external video display, external artificial lighting, rapid changes between light and dark, as when driving through shadows cast by tree branches, or any other external light source. The wearable computing device 100 may analyze data received from the ambient light sensor 140 to determine whether such flickering or pulsating lights are present and thus determine that a potential seizure-inducing condition is present.

In block 412, the wearable computing device 100 determines whether a physiological condition such as nausea, seizure, or potential seizure has been detected in the sensor data. If no physiological condition has been detected, the method 400 loops back to block 402 to continue monitoring sensor data. If a physiological condition has been detected, the method 400 advances to block 414.

In block 414, the wearable computing device 100 applies a mitigation strategy appropriate for the detected physiological condition. The particular mitigation strategy applied may depend on the physiological condition detected. In some embodiments, the wearable computing device 100 may apply multiple mitigation strategies, contemporaneously or sequentially. Because, as described above, the physiological condition may be detectable in advance of the user showing overt signs of the physiological condition, the mitigation strategy may help prevent the onset of user-noticeable symptoms.

In some embodiments, in block 416 the wearable computing device 100 suspends display updates on the head-mounted display 132 until the wearable computing device 100 detects that the user has stopped moving. The wearable computing device 100 may poll the motion detector(s) 136 and suspend display updates until data received from the motion detector(s) 136 indicate that the wearable computing device 100 is at rest. While in motion, the head-mounted display 132 may display a frozen or still image or may display no image at all. Nausea and/or seizures may be mitigated by eliminating differences and/or lag between motion depicted by the head-mounted display 132 and actual motion of the user. Thus, this mitigation strategy is likely appropriate for embodiments wherein the motion sensor(s)

138 are mounted with the head-mounted display 132 on the user's head, such as the smart eyeglasses illustrated in FIG. 2

In some embodiments, in block 418 the wearable computing device 100 reduces display overlay density. That is, the wearable computing device 100 reduces the number and/or informational density of display overlays on the head-mounted display 132. Similarly, in some embodiments, in block 420 the wearable computing device 100 may hide all display overlays on the head-mounted display 132. In some embodiments, in block 422 the wearable computing device 100 may reduce the intensity or color saturation of display overlays on the head-mounted display 132. In some embodiments, in block 424 the wearable computing device 100 may reduce the resolution of the display overlays. For example, the wearable computing device 100 may blur or pixelate display overlays on the head-mounted display 132. Reducing and/or eliminating display density, intensity, saturation, and resolution all tend to decrease cognitive confusion for the user, and thus tend to mitigate physiological conditions such as nausea and/or seizure.

In some embodiments, in block 426, the wearable computing device 100 may limit display in the head-mounted display 132 to one eye of the user. Displaying in one eye only may particularly mitigate seizures. For example, a stereoscopic head-mounted display 132 may ordinarily display images to both eyes of the user. The wearable computing device 100 may suspend display in one eye while allowing display in the other eye to mitigate seizure and/or nausea. Of course, this mitigation strategy is not applicable for wearable computing devices with a head-mounted display 132 that ordinarily displays images for one eye only, such as the smart eyeglasses of FIG. 2. Displaying images in one eye only additionally eliminates the stereoscopic three-dimensional effect, which may also reduce nausea. Accordingly, in some embodiments the wearable computing device 100 may eliminate any three-dimensional viewing effect, for example by displaying the same image to both eyes of a stereoscopic head-mounted display 132.

In some embodiments, in block 428 the wearable computing device 100 may reduce the intensity of environmental light admitted through the head-mounted display 132 by adjusting the variable lenses 134. For example, the wearable computing device 100 may close active shutters, darken adjustable tinting, or otherwise reduce light transmission through the variable lenses 134. Reducing environmental light may be appropriate for a potential seizure condition detected based on data from the ambient light sensor 140. As with display overlays discussed above, reducing the intensity of light reaching the user's eye may mitigate nausea and/or seizure.

After applying the mitigation strategy, in block 430 in some embodiments the wearable computing device 100 updates the risk factors database 312 based on the detected physical condition. The risk factors database 312 may be updated with the particular sensor data associated with the detected physical condition. Recording sensor data may allow the risk factors database 312 to adapt to the characteristics of a particular user over time, and may allow the wearable computing device 100 to predict and prevent the physiological condition in the future, as further described below. After applying the mitigation strategy and in some embodiments updating the risk factors database 312, the method 400 loops back to block 402 to continue monitoring the sensor data.

Figure 5:
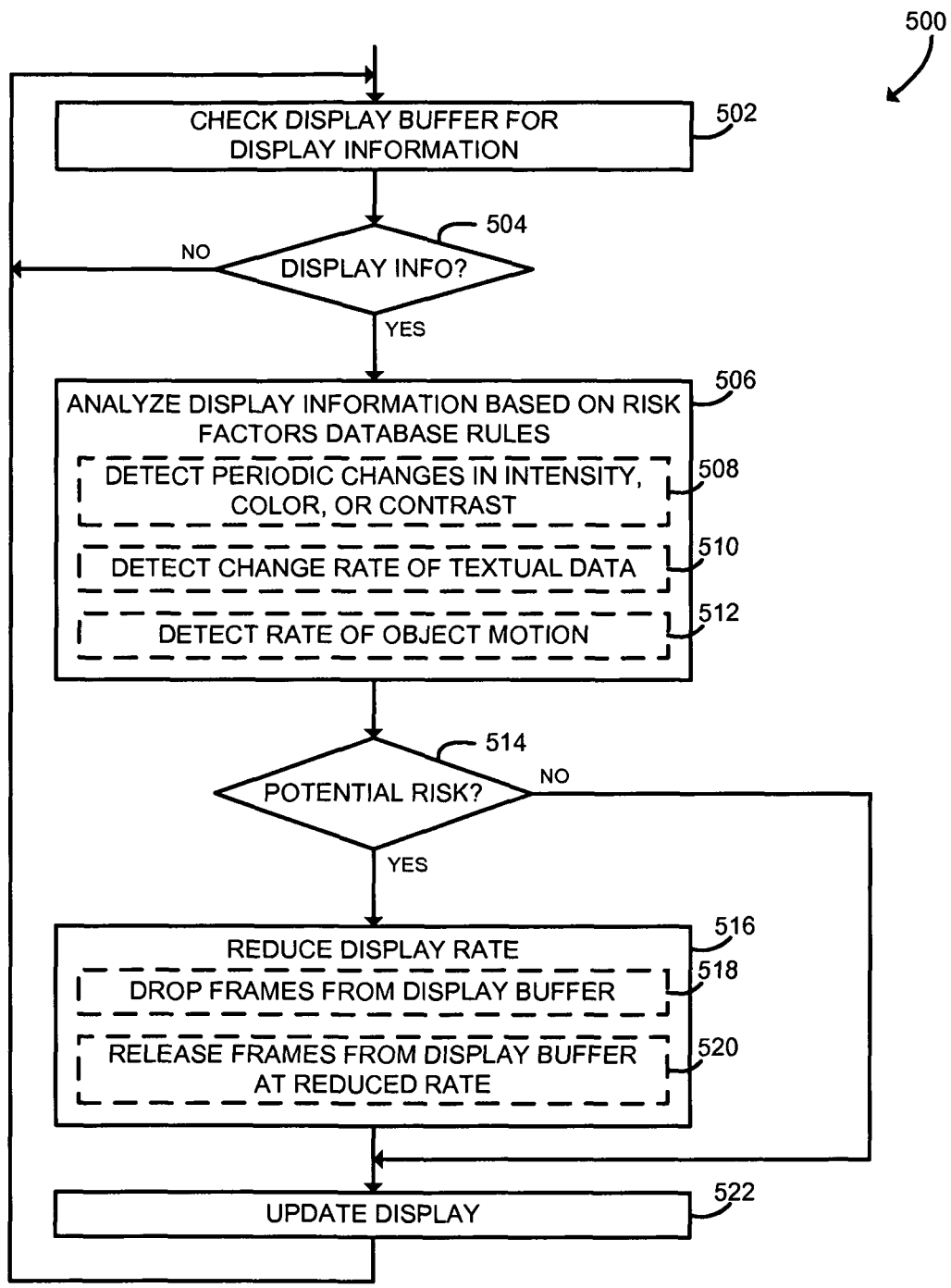
FIG. 5 is a simplified flow diagram of at least one embodiment of a method for reducing potential risk to a user of a head-mounted display, which may be executed by the computing device of FIGS. 1-3.

Referring now to FIG. 5, in use, the wearable computing device 100 may execute a method 500 for reduction of potential risk to the user. In some embodiments, the method 500 may be executed contemporaneously, or in parallel, with the method 400. The method 500 begins with block 502, in which the wearable computing device 100 checks the display buffer 126 for display information. As described above, display information stored in the display buffer 126 may include display frames that are to be displayed on the head-mounted display 132. The display information may be generated by one or more user applications executing on the wearable computing device 100. In block 504, the wearable computing device 100 determines whether display information is present. If not, the method 500 loops back to block 502 to continue monitoring for display information. If display information is present, the method 500 advances to block 506.

In block 506, the wearable computing device 100 analyzes the display information based on rules contained in the risk factors database 312. The risk factors database 312 may include rules generally applicable to a large portion of the population. For example, the risk factors database 312 may include rules for visual flashing frequencies known to cause a high risk of seizure in the population. The risk factors database 312 may also describe the rate at which information may be visually consumed by the user. In other embodiments, the risk factors database 312 may include rules tailored to the particular user. Such rules may be supplied manually, or may be automatically updated based on detected physiological conditions, as described above in connection with block 430 of FIG. 4.

In some embodiments, in block 508, the wearable computing device 100 may analyze the display information for periodic changes in display intensity, contrast, or color in order to identify "flickering" or pulsating images that may cause seizures. The wearable computing device 100 may also analyze the display information for particular visual patterns associated with risk to the user. The rules of the risk factors database 312 may describe the particular periodic changes and/or visual patterns associated with risk to the user. In some embodiments, in block 510, the wearable computing device 100 detects a change rate of textual data. In some embodiments, the wearable computing device 100 may detect the rate of change of the display information without detecting or interpreting any text. In such embodiments, the wearable computing device 100 may thus detect quick flashes of text. Such rapid information flashes may occur when several applications attempt to post updates to the head-mounted display 132 in quick succession. In other embodiments, the wearable computing device 100 may perform more complicated text recognition to determine the amount of text displayed and the rate at which it is displayed, e.g., the rate that text is scrolled on the screen. In some embodiments, in block 512 the wearable computing device 100 may determine a rate of object motion, that is, the apparent speed of an object represented in the display information.

In block 514, the wearable computing device 100 determines whether the display information presents potential risk to the user, based on the rules of the risk factors database 312. For example, the wearable computing device 100 may determine that the periodic changes of the display information present potential risk of seizure. As another example, the wearable computing device 100 may determine that information is being displayed at a rate that may exceed the rate at which information is consumable by humans, based on the change rate of textual data and/or the rate of object motion detected in the display information. As described above, the risk factors database 312 contains the parameters used to determine whether the display information presents the potential risk to the user. If no potential risk to the user is presented, the method 500 branches to block 522, described below. If potential risk is presented, the method 500 advances to block 516.

In block 516, the wearable computing device 100 reduces the display update rate to a safe and/or consumable rate. Reducing the display update rate reduces the rate at which information is displayed on the head-mounted display 132. The display update rate may be adjusted independently of any hardware refresh rate of the head-mounted display 132. The wearable computing device 100 may reduce display flashing or pulsating to a low frequency that does not create potential for seizures. In other embodiments, the wearable computing device 100 may reduce the display rate to allow information displayed to be read or otherwise consumed by the user. As described above, the maximum safe and/or consumable display update rates may be stored in the risk factors database 312. In some embodiments, in block 518, the wearable computing device 100 reduces the display rate by dropping one or more frames from the display buffer 126. Dropping frames may reduce flicker and/or pulsation by reducing the frequency that displayed images are changed. Of course, dropped frames are not displayed to the user and thus may cause information to be lost. Rather than dropping frames, in some embodiments, the wearable computing device 100 may blend, mix, or otherwise combine adjacent frames from the display buffer 126 to lose less information and retain the original display timing. In some embodiments, in block 520 the wearable computing device 100 releases one or more frames from the display buffer 126 for display at a reduced rate below the maximum safe and/or consumable rate. Releasing the frames for display at a slower rate effectively runs the display in "slow motion," thereby reducing flashing and/or pulsation. Additionally, because all frames are displayed, no information is lost. However, because all frames are to be displayed, sufficient space for the frames must be available in the display buffer 126 and/or any associated backing store.

In block 522, the wearable computing device 100 updates the head-mounted display 132 with the display information. As described above, the display information is either displayed at its original update rate if below the maximum safe and/or consumable rate, or is displayed at a reduced rate. Thus, the display information has been effectively filtered according to rules in the risk factors database 312. After displaying the display information, the method 500 loops back to block 502 to continue updating display information.

EXAMPLES

Illustrative examples of the technologies disclosed herein are provided below. An embodiment of the technologies may include any one or more, and any combination of, the examples described below.

Example 1 includes a wearable computing device for mitigating a physiological condition of a user, the wearable computing device comprising a head-mounted display to display one or more display overlays; one or more sensors to produce sensor data indicative of one or more physical attributes of the user; a physiological monitoring module to (i) receive the sensor data from the one or more sensors while the head-mounted display displays the display overlays and (ii) analyze the sensor data to detect a physiological condition of the user; and a risk mitigation module to apply a mitigation strategy to mitigate the physiological condition in response to detection of the physiological condition.

Example 2 includes the subject matter of Example 1, and wherein the one or more sensors comprises at least one of: an accelerometer, a gyroscope, a compass, an eye tracking sensor, a galvanic skin response sensor, a pulse sensor, or a thermometer.

Example 3 includes the subject matter of any of Examples 1 and 2, and wherein the physiological monitoring module is further to detect a nausea condition of the user based on analysis of the sensor data.

Example 4 includes the subject matter of any of Examples 1-3, and wherein the physiological monitoring module further to detect a seizure condition of the user based on analysis of the sensor data.

Example 5 includes the subject matter of any of Examples 1-4, and wherein the mitigation strategy comprises to suspend updating of the head-mounted display while the head-mounted display is moving.

Example 6 includes the subject matter of any of Examples 1-5, and wherein the mitigation strategy comprises to reduce a number of display overlays displayed by the head-mounted display.

Example 7 includes the subject matter of any of Examples 1-6, and wherein the mitigation strategy comprises to reduce intensity, color saturation, or contrast of a display overlay of the head-mounted display.

Example 8 includes the subject matter of any of Examples 1-7, and wherein the mitigation strategy comprises to reduce a resolution of a display overlay of the head-mounted display.

Example 9 includes the subject matter of any of Examples 1-8, and wherein the mitigation strategy comprises to suspend display of the head-mounted display to one eye of the user while display to the other eye of the user is allowed.

Example 10 includes the subject matter of any of Examples 1-9, and wherein the one or more sensors comprises an ambient light sensor; the head-mounted display comprises a variable lens; the physiological monitoring module is further to detect a potential seizure condition of the user based on analysis of the sensor data received from the ambient light sensor; and the wearable computing device further comprises a lens control module to reduce an intensity of environmental light admitted through the variable lens in response to detection of the potential seizure condition.

Example 11 includes the subject matter of any of Examples 1-10, and further including a frame configured to be worn on the user's face; and a pair of lenses coupled to the frame and, when worn on the user's face, positioned in front of the user's eyes; wherein the head-mounted display and the one or more sensors are coupled to the frame.

Example 12 includes a wearable computing device for reducing potential risk to a user, the wearable computing device comprising a head-mounted display to display information to the user; a display module to buffer display information to be displayed by the head-mounted display; a risk prediction module to analyze the buffered display information based on a rule policy of a risk factors database to determine whether the display information presents a potential risk to the user; and a risk mitigation module to reduce a display rate of the head-mounted display in response to a determination that the potential risk to the user exists.

Example 13 includes the subject matter of Example 12, and wherein to analyze the buffered display information comprises to analyze the buffered display information for periodic changes in display intensity, display color, or display contrast.

Example 14 includes the subject matter of any of Examples 12 and 13, and wherein to analyze the buffered display information further comprises to determine whether the periodic changes present a potential risk for seizure.

Example 15 includes the subject matter of any of Examples 12-14, and wherein to determine whether the periodic changes present the potential risk for seizure comprises to determine whether a rate of the periodic changes is between five Hz and thirty Hz.

Example 16 includes the subject matter of any of Examples 12-15, and wherein to analyze the buffered display information comprises to analyze a change rate of textual data presented by the display information; and to determine whether the potential risk to the user exists comprises to determine whether the change rate of the textual data exceeds a maximum information transfer rate.

Example 17 includes the subject matter of any of Examples 12-16, and wherein to analyze the buffered display information comprises to analyze a speed of an object presented by the display information; and to determine whether the potential risk to the user exists comprises to determine whether the speed of the object exceeds a maximum perceivable speed.

Example 18 includes the subject matter of any of Examples 12-17, and wherein the risk prediction module is further to update the rule policy of the risk factors database based on the user of the head-mounted display.

Example 19 includes the subject matter of any of Examples 12-18, and wherein to reduce the display rate comprises to drop one or more frames of the buffered display information.

Example 20 includes the subject matter of any of Examples 12-19, and wherein to reduce the display rate comprises to blend two or more adjacent frames of the buffered display information.

Example 21 includes the subject matter of any of Examples 12-20, and wherein to reduce the display rate comprises to release one or more frames of the buffered display information at a reduced rate.

Example 22 includes the subject matter of any of Examples 12-21, and further including a frame configured to be worn on the user's face; and a pair of lenses coupled to the frame and, when worn on the user's face, positioned in front of the user's eyes; wherein the head-mounted display is coupled to the frame.

Example 23 includes a method for mitigating a physiological condition using a wearable computing device, the method comprising displaying, by the wearable computing device, one or more display overlays using a head-mounted display of the wearable computing device; receiving, by the wearable computing device, sensor data from one or more sensors coupled to the wearable computing device while displaying the display overlays, the sensor data indicative of one or more physical attributes of a user of the wearable computing device; analyzing, by the wearable computing device, the sensor data to detect a physiological condition of the user; and applying, by the wearable computing device, a mitigation strategy to mitigate the physiological condition in response to detecting the physiological condition.

Example 24 includes the subject matter of Example 23, and wherein receiving the sensor data comprises receiving sensor data from: an accelerometer, a gyroscope, a compass, an eye tracking sensor, a galvanic skin response sensor, a pulse sensor, or a thermometer.

Example 25 includes the subject matter of any of Examples 23 and 24, and wherein analyzing the sensor data comprises detecting a nausea condition of the user based on analysis of the sensor data.

Example 26 includes the subject matter of any of Examples 23-25, and wherein analyzing the sensor data comprises detecting a seizure condition of the user based on analysis of the sensor data.

Example 27 includes the subject matter of any of Examples 23-26, and wherein applying the mitigation strategy comprises suspending updating of the head-mounted display while the head-mounted display is moving.

Example 28 includes the subject matter of any of Examples 23-27, and wherein applying the mitigation strategy comprises reducing a number of display overlays displayed by the head-mounted display.

Example 29 includes the subject matter of any of Examples 23-28, and wherein applying the mitigation strategy comprises reducing intensity, color saturation, or contrast of a display overlay of the head-mounted display.

Example 30 includes the subject matter of any of Examples 23-29, and wherein applying the mitigation strategy comprises reducing a resolution of a display overlay of the head-mounted display.

Example 31 includes the subject matter of any of Examples 23-30, and wherein applying the mitigation strategy comprises suspending display of the head-mounted display to one eye of the user while allowing display to the other eye of the user.

Example 32 includes the subject matter of any of Examples 23-31, and wherein receiving the sensor data comprises receiving sensor data from an ambient light sensor; analyzing the sensor data comprises detecting a potential seizure condition of the user based on analysis of the sensor data received from the ambient light sensor; and applying the mitigation strategy comprises reducing an intensity of environmental light admitted through a variable lens of the head-mounted display.

Example 33 includes a method for reducing potential risk to a user of a head-mounted display, the method comprising buffering, by a wearable computing device, display information to be displayed by a head-mounted display of the wearable computing device; analyzing, by the wearable computing device, the buffered display information based on a rule policy of a risk factors database to determine whether the display information presents a potential risk to the user; and reducing, by the wearable computing device, a display rate of the head-mounted display in response to determining the display information presents the potential risk to the user.

Example 34 includes the subject matter of Example 33, and wherein analyzing the buffered display information comprises analyzing the buffered display information for periodic changes in display intensity, display color, or display contrast.

Example 35 includes the subject matter of any of Examples 33 and 34, and wherein analyzing the buffered display information further comprises determining whether the periodic changes present a potential risk for seizure.

Example 36 includes the subject matter of any of Examples 33-35, and wherein determining whether the periodic changes present the potential risk for seizure comprises determining whether a rate of the periodic changes is between five Hz and thirty Hz.

Example 37 includes the subject matter of any of Examples 33-36, and wherein analyzing the buffered display information comprises analyzing a change rate of textual data presented by the display information; and determining whether the potential risk to the user exists comprises determining whether the change rate of the textual data exceeds a maximum information transfer rate.

Example 38 includes the subject matter of any of Examples 33-37, and wherein analyzing the buffered display information comprises analyzing a speed of an object presented by the display information; and determining whether the potential risk to the user exists comprises determining whether the speed of the object exceeds a maximum perceivable speed.

Example 39 includes the subject matter of any of Examples 33-38, and further including updating the rule policy of the risk factors database based on the user of the head-mounted display.

Example 40 includes the subject matter of any of Examples 33-39, and wherein reducing the display rate comprises dropping one or more frames of the buffered display information.

Example 41 includes the subject matter of any of Examples 33-40, and wherein reducing the display rate comprises blending two or more adjacent frames of the buffered display information.

Example 42 includes the subject matter of any of Examples 33-41, and wherein reducing the display rate comprises releasing one or more frames of the buffered display information at a reduced rate.

Example 43 includes a computing device comprising a processor; and a memory having stored therein a plurality of instructions that when executed by the processor cause the computing device to perform the method of any of Examples 23-42.

Example 44 includes one or more machine readable storage media comprising a plurality of instructions stored thereon that in response to being executed result in a wearable computing device performing the method of any of Examples 23-42.

Example 45 includes a wearable computing device comprising means for performing the method of any of Examples 23-42.

The invention claimed is:

1. A wearable computing device for mitigating a physiological condition of a user, the wearable computing device comprising:
   a head-mounted display to display one or more display overlays, wherein the head-mounted display comprises a variable lens;
   one or more sensors to produce sensor data indicative of one or more physical attributes of the user, wherein the one or more sensors comprises an ambient light sensor;
   a physiological monitoring module to (i) receive the sensor data from the one or more sensors while the head-mounted display displays the display overlays, (ii) analyze the sensor data to detect a physiological condition of the user, and (iii) detect a potential seizure condition of the user based on analysis of the sensor data received from the ambient light sensor;
   a risk mitigation module to apply a mitigation strategy to mitigate the physiological condition in response to detection of the physiological condition; and
   a lens control module to reduce an intensity of environmental light admitted through the variable lens in response to detection of the potential seizure condition.

2. The wearable computing device of claim 1, wherein the physiological monitoring module is further to detect a nausea condition of the user based on analysis of the sensor data.

3. The wearable computing device of claim 1, wherein the physiological monitoring module further to detect a seizure condition of the user based on analysis of the sensor data.

4. The wearable computing device of claim 1, wherein the mitigation strategy comprises to suspend updating of the head-mounted display while the head-mounted display is moving.

5. The wearable computing device of claim 1, wherein the mitigation strategy comprises to reduce a number of display overlays displayed by the head-mounted display.

6. The wearable computing device of claim 1, wherein the mitigation strategy comprises to reduce one of: intensity, color saturation, or contrast of a display overlay of the head-mounted display.

7. The wearable computing device of claim 1, wherein the mitigation strategy comprises to reduce a resolution of a display overlay of the head-mounted display.

8. The wearable computing device of claim 1, further comprising:
   a frame configured to be worn on the user's face; and
   a pair of lenses coupled to the frame and, when worn on the user's face, positioned in front of the user's eyes;
   wherein the head-mounted display and the one or more sensors are coupled to the frame.

9. A wearable computing device for reducing potential risk to a user, the wearable computing device comprising:
   a head-mounted display to display information to the user;
   a display module to buffer display information to be displayed by the head-mounted display;
   a risk prediction module to analyze the buffered display information based on a rule policy of a risk factors database to determine whether the display information presents a potential risk to the user, wherein to analyze the buffered display information comprises to (i) analyze the buffered display information for periodic changes in display intensity, display color, or display contrast and (ii) determine whether the periodic changes present a potential risk for seizure; and
   a risk mitigation module to reduce a display rate of the head-mounted display in response to a determination that the potential risk to the user exists.

10. The wearable computing device of claim 9, wherein:
    to analyze the buffered display information comprises to analyze a change rate of textual data presented by the display information; and
    to determine whether the potential risk to the user exists comprises to determine whether the change rate of the textual data exceeds a maximum information transfer rate.

11. The wearable computing device of claim 9, wherein:
    to analyze the buffered display information comprises to analyze a speed of an object presented by the display information; and
    to determine whether the potential risk to the user exists comprises to determine whether the speed of the object exceeds a maximum perceivable speed.

12. The wearable computing device of claim 9, wherein the risk prediction module is further to update the rule policy of the risk factors database based on the user of the head-mounted display.

13. The wearable computing device of claim 9, wherein to reduce the display rate comprises to drop one or more frames of the buffered display information.

14. The wearable computing device of claim 9, wherein to reduce the display rate comprises to blend two or more adjacent frames of the buffered display information.

15. The wearable computing device of claim 9, wherein to reduce the display rate comprises to release one or more frames of the buffered display information at a reduced rate.

16. The wearable computing device of claim 9, further comprising:
a frame configured to be worn on the user's face; and
a pair of lenses coupled to the frame and, when worn on the user's face, positioned in front of the user's eyes;
wherein the head-mounted display is coupled to the frame.

17. One or more non-transitory, computer-readable storage media comprising a plurality of instructions that in response to being executed cause a wearable computing device to:
display one or more display overlays using a head-mounted display of the wearable computing device;
receive sensor data from one or more sensors coupled to the wearable computing device while displaying the display overlays, the sensor data indicative of one or more physical attributes of a user of the wearable computing device, wherein the one or more sensors comprises an ambient light sensor;
analyze the sensor data to detect a physiological condition of the user, wherein to analyze the sensor data comprises to detect a potential seizure condition of the user based on analysis of the sensor data received from the ambient light sensor; and
apply a mitigation strategy to mitigate the physiological condition in response to detecting the physiological condition, wherein to apply the mitigation strategy comprises to reduce an intensity of environmental light admitted through a variable lens of the head-mounted display in response to detection of the potential seizure condition.

18. The one or more non-transitory, computer-readable storage media of claim 17, wherein to analyze the sensor data comprises to detect a nausea condition of the user based on analysis of the sensor data.

19. The one or more non-transitory, computer-readable storage media of claim 17, wherein to analyze the sensor data comprises to detect a seizure condition of the user based on analysis of the sensor data.

20. One or more non-transitory, computer-readable storage media comprising a plurality of instructions that in response to being executed cause a wearable computing device to:
buffer display information to be displayed by a head-mounted display of the wearable computing device;
analyze the buffered display information based on a rule policy of a risk factors database to determine whether the display information presents a potential risk to the user, wherein to analyze the buffered display information comprises to (i) analyze the buffered display information for periodic changes in display intensity, display color, or display contrast and (ii) determine whether the periodic changes present a potential risk for seizure; and
reduce a display rate of the head-mounted display in response to determining the display information presents the potential risk to the user.

21. The one or more non-transitory, computer-readable storage media of claim 20, wherein:
to analyze the buffered display information comprises to analyze a change rate of textual data presented by the display information; and
to determine whether the potential risk to the user exists comprises to determine whether the change rate of the textual data exceeds a maximum information transfer rate.

22. The one or more non-transitory, computer-readable storage media of claim 20, wherein:
to analyze the buffered display information comprises to analyze a speed of an object presented by the display information; and
to determine whether the potential risk to the user exists comprises to determine whether the speed of the object exceeds a maximum perceivable speed.

23. A method for mitigating a physiological condition while using a wearable computing device, the method comprising:
displaying, by the wearable computing device, one or more display overlays using a head-mounted display of the wearable computing device;
receiving, by the wearable computing device, sensor data from one or more sensors coupled to the wearable computing device while displaying the display overlays, the sensor data indicative of one or more physical attributes of a user of the wearable computing device, wherein the one or more sensors comprises an ambient light sensor;
analyzing, by the wearable computing device, the sensor data to detect a physiological condition of the user, wherein analyzing the sensor data comprises detecting a potential seizure condition of the user based on analysis of the sensor data received from the ambient light sensor; and
applying, by the wearable computing device, a mitigation strategy to mitigate the physiological condition in response to detecting the physiological condition, wherein applying the mitigation strategy comprises reducing an intensity of environmental light admitted through a variable lens of the head-mounted display in response to detecting the potential seizure condition.

24. The method of claim 23, wherein applying the mitigation strategy comprises:
suspending updating of the head-mounted display while the head-mounted display is moving;
reducing a number of display overlays displayed by the head-mounted display;
reducing intensity, color saturation, or contrast of a display overlay of the head-mounted display; or
reducing a resolution of a display overlay of the head-mounted display.

25. A method for reducing potential risk to a user of a head-mounted display, the method comprising:
buffering, by a wearable computing device, display information to be displayed by a head-mounted display of the wearable computing device;
analyzing, by the wearable computing device, the buffered display information based on a rule policy of a risk factors database to determine whether the display information presents a potential risk to the user, wherein analyzing the buffered display information comprises: (i) analyzing the buffered display information for periodic changes in display intensity, display color, or display contrast and (ii) determining whether the periodic changes present a potential risk for seizure; and
reducing, by the wearable computing device, a display rate of the head-mounted display in response to determining the display information presents the potential risk to the user.

* * * * *